(12) United States Patent
Thompson et al.

(10) Patent No.: US 7,938,115 B2
(45) Date of Patent: May 10, 2011

(54) CARDIOPULMONARY RESUSCITATION DEVICE

(76) Inventors: Darrell K. Thompson, Memphis, TN (US); Phyllis D. Thompson, Memphis, TN (US)

( * ) Notice: Subject to any disclaimer, the term of this patent is extended or adjusted under 35 U.S.C. 154(b) by 0 days.

(21) Appl. No.: 12/709,018

(22) Filed: Feb. 19, 2010

(65) Prior Publication Data

US 2010/0206315 A1 Aug. 19, 2010

Related U.S. Application Data

(60) Division of application No. 11/327,278, filed on Jan. 6, 2006, now Pat. No. 7,806,118, which is a continuation-in-part of application No. 10/820,239, filed on Apr. 6, 2004, now Pat. No. 7,032,596.

(51) Int. Cl.
| | |
|---|---|
| A61M 16/00 | (2006.01) |
| A61M 11/00 | (2006.01) |
| A61M 15/08 | (2006.01) |
| A62B 9/02 | (2006.01) |
| A62B 18/02 | (2006.01) |
| A61H 1/00 | (2006.01) |
| A61H 31/00 | (2006.01) |
| A61H 7/00 | (2006.01) |
| A61H 23/00 | (2006.01) |

(52) U.S. Cl. ......... 128/205.13; 128/202.28; 128/202.29; 128/203.11; 128/200.22; 128/205.14; 128/205.17; 128/205.24; 128/205.25; 128/203.28; 128/203.29; 128/204.12; 601/1; 601/41; 601/42; 601/44; 601/84; 601/94; 601/107; 601/134; 601/135

(58) Field of Classification Search ............. 128/202.28, 128/202.29, 203.11, 200.22, 205.13, 205.14, 128/205.17, 205.24, 205.25, 203.28, 203.29, 204.12; 601/1, 41, 42, 44, 84, 94, 107, 134, 135

See application file for complete search history.

(56) References Cited

U.S. PATENT DOCUMENTS

| | | | | |
|---|---|---|---|---|
| 3,046,978 | A | * | 7/1962 | Lea ........................... 128/205.13 |
| 3,809,079 | A | * | 5/1974 | Buttaravoli .............. 128/206.24 |
| 3,882,860 | A | | 5/1975 | Frimberger |
| 4,374,521 | A | | 2/1983 | Nelson et al. |
| 4,440,163 | A | | 4/1984 | Spergel |
| 4,532,923 | A | | 8/1985 | Flynn |
| 4,821,712 | A | | 4/1989 | Gossett |

(Continued)

FOREIGN PATENT DOCUMENTS

WO PCT/US07/00453 10/2007

*Primary Examiner* — Patricia M Bianco
*Assistant Examiner* — Nihir Patel
(74) *Attorney, Agent, or Firm* — Walker, McKenzie & Walker, P.C.

(57) ABSTRACT

A cardiopulmonary resuscitation device that combines ventilation of a patient's lungs with chest compressions on the patient's sternum area. The device includes a self-inflating bag having an outlet port through which the content of the bag is forced when bag is compressed; target indicia on the bag to indicate the proper position of the bag on the patient's sternum area and to indicate the proper location on the bag for applying force to the top side thereof; a face mask for placement over the patient's mouth and nose; and a tube extending from the bag to the face mask. The device may include indicia for indicating the amount of pressure applied to the self-inflating bag, and a backboard including belt/motor structure for providing repeated and rapid chest compression and forced ventilation of the patient's lungs.

7 Claims, 8 Drawing Sheets

U.S. PATENT DOCUMENTS

| | | |
|---|---|---|
| 4,919,132 A | 4/1990 | Miser |
| D321,418 S | 11/1991 | Dolida et al. |
| 5,163,424 A | 11/1992 | Køhnke |
| D335,552 S | 5/1993 | Kohnke |
| 5,427,091 A | 6/1995 | Phillips |
| 5,483,955 A | 1/1996 | Morris |
| 5,492,114 A | 2/1996 | Vroman |
| 5,540,221 A | 7/1996 | Kaigler et al. |
| 5,557,049 A | 9/1996 | Ratner |
| 5,647,354 A | 7/1997 | Lakhani et al. |
| 5,787,880 A | 8/1998 | Swanson et al. |
| 5,791,340 A | 8/1998 | Schleufe et al. |
| 5,803,074 A | 9/1998 | Pope |
| 5,842,467 A | 12/1998 | Greco |
| 5,996,579 A | 12/1999 | Coates et al. |
| 6,058,933 A | 5/2000 | Good et al. |
| 6,062,219 A | 5/2000 | Lurie et al. |
| 6,098,621 A | 8/2000 | Esnouf |
| 6,123,075 A | 9/2000 | Kirk |
| 6,155,257 A | 12/2000 | Lurie et al. |
| 6,276,363 B1 | 8/2001 | Gray |
| 6,340,023 B2 | 1/2002 | Elkins |
| 6,527,011 B1 | 3/2003 | Mantz |
| 6,539,941 B2 | 4/2003 | Haubeil |
| 6,568,388 B2 | 5/2003 | Christopher |
| 6,578,574 B1 | 6/2003 | Køhnke |
| 6,631,713 B1 | 10/2003 | Christopher |
| 6,745,769 B2 | 6/2004 | Klempau |
| 6,763,831 B2 | 7/2004 | Sniadach |
| 6,776,160 B2 | 8/2004 | Wang |
| 6,792,947 B1 | 9/2004 | Bowden |
| 6,988,499 B2 | 1/2006 | Holt et al. |
| 7,056,296 B2 | 6/2006 | Sherman et al. |
| 7,226,427 B2 | 6/2007 | Steen |
| 2004/0089296 A1* | 5/2004 | Bowden .................. 128/203.12 |

* cited by examiner

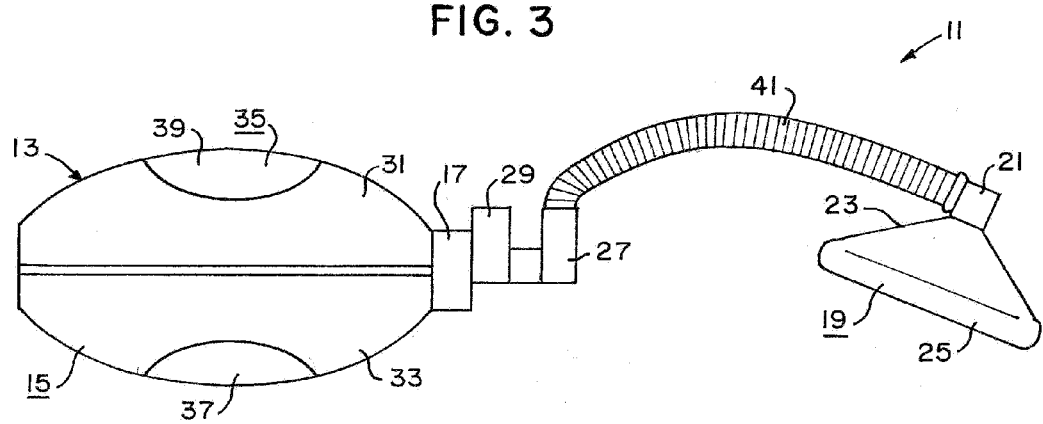
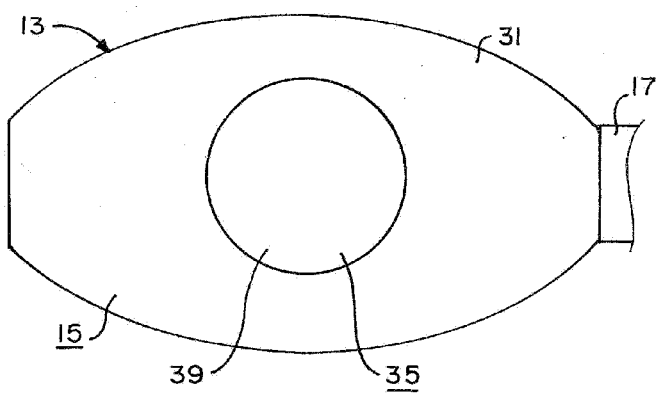
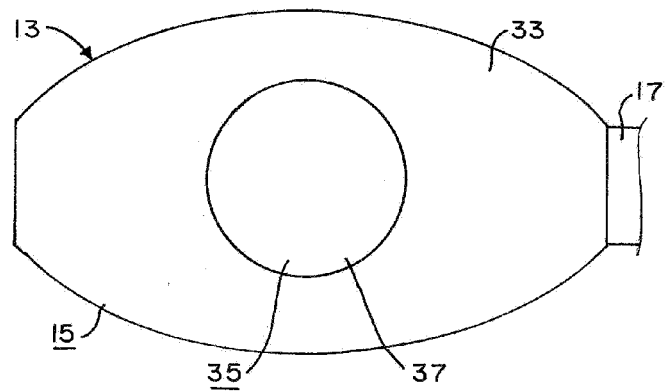

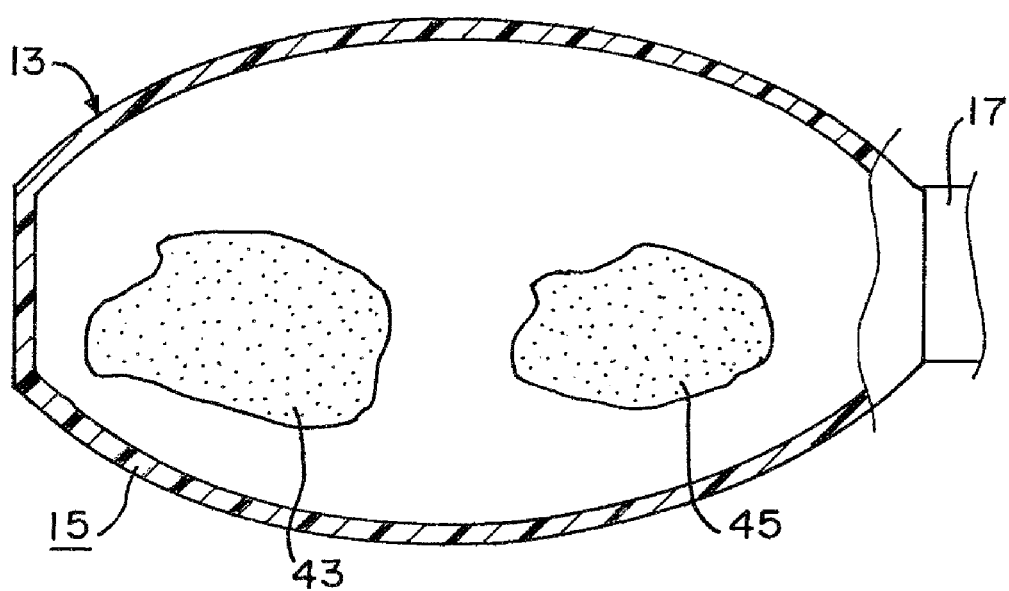

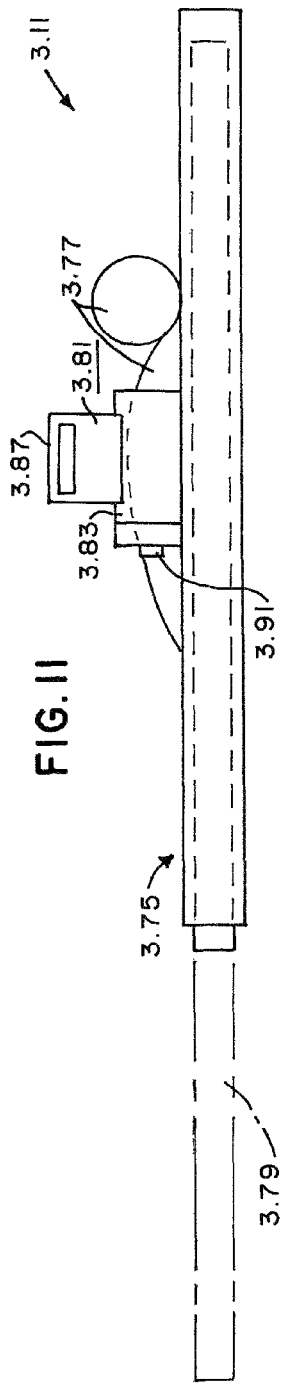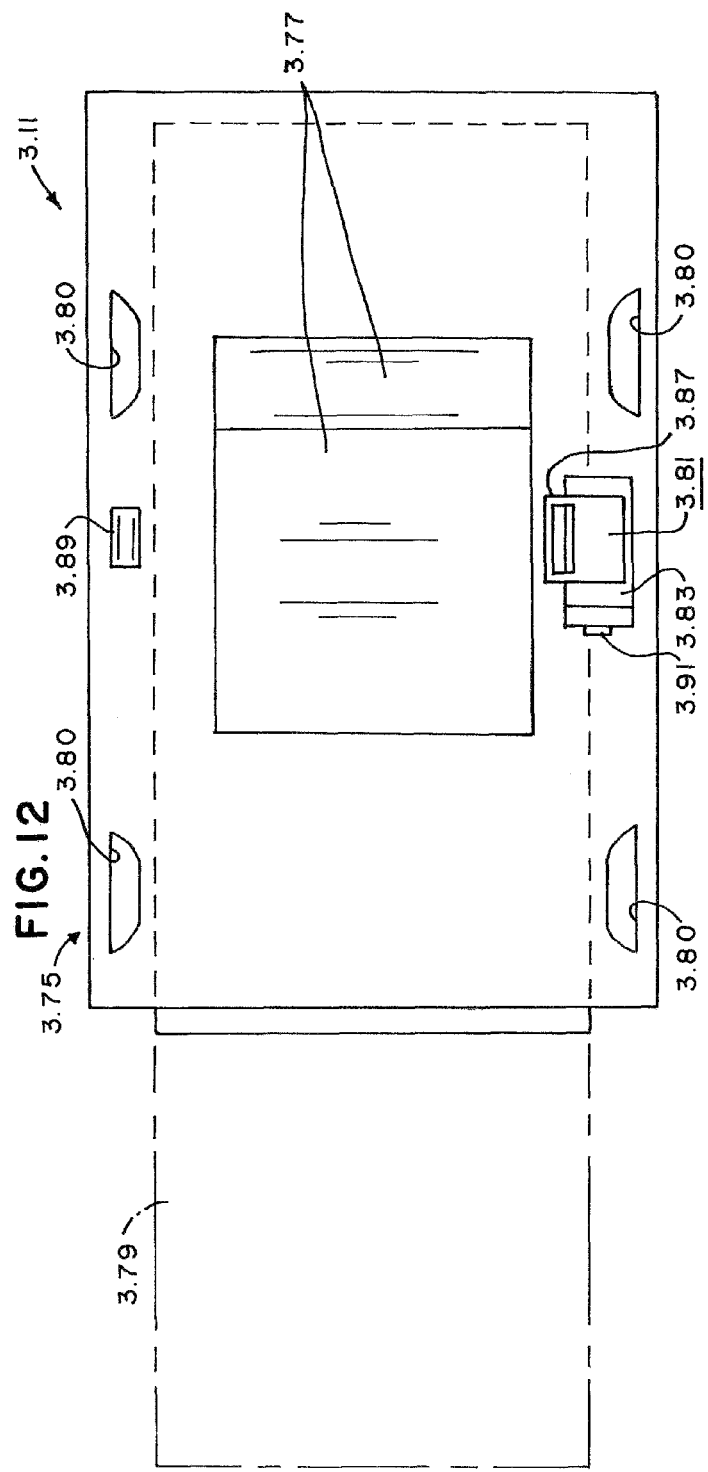

CARDIOPULMONARY RESUSCITATION DEVICE

CROSS REFERENCE TO RELATED APPLICATION

This application is a division, and claims priority benefit, of U.S. patent application Ser. No. 11/327,278 (filed Jan. 6, 2006) entitled Cardiopulmonary Resuscitation Device, which issued as U.S. Pat. No. 7,806,118 on Oct. 5, 2010, which itself was a continuation-in-part, and claims priority benefit as does the instant application, of U.S. patent application Ser. No. 10/820,239 (filed Apr. 6, 2004) entitled Cardiopulmonary Resuscitation Device and Method, which issued as U.S. Pat. No. 7,032,596 on Apr. 25, 2006.

BACKGROUND OF THE INVENTION

1. Field of the Invention

The present invention relates, in general, to a device that uses a squeeze bag-type resuscitator in a manner that incorporates cardiopulmonary resuscitation (CPR) type chest compressions.

2. Background Art

Two general emergency procedures used when a patient's normal breathing has been disrupted are the use of self-inflating, squeeze bag resuscitators and cardiopulmonary resuscitation (CPR).

Self-inflating, squeeze bag resuscitators are commonly used for artificial, emergency ventilation of a patient's lungs to revive the patient when normal breathing has been disrupted, but the patient's heart is still beating. Several types of such self-inflating, squeeze bag resuscitators are in wide use, and are sometimes referred to as respirators. The typical self-inflating, squeeze bag resuscitator consists, in general, of an airtight face mask that fits over the patient's nose and mouth, and a self-inflating bag connected to the face mask. When the bag is squeezed, air or oxygen is forced from the bag into the patient's lungs. The bag re-inflates automatically when released, drawing atmosphere air, etc., into the bag through a bag fill valve (a one way, inward flow check valve) typically located either between the bag and face mask or at the end of the bag opposite from the face mask. Air from the lungs leaves the mask by some type of escape valve (often referred to as a nonrebreathing or NRB valve) without returning to the bag.

Cardiopulmonary resuscitation (CPR) is administered when a patient stops breathing and the patient's heart stops beating, due to sudden cardiac arrest or the like. CPR includes mouth-to-mouth breathing, and chest compression. To perform mouth-to-mouth breathing, the patient's nose is pinched shut and the rescuer blows directly into the patient's mouth. After mouth-to-mouth breathing, the rescuer then performs chest compression by pushing down on the patient's chest right between the nipples (i.e., the sternum area).

Nothing in the known prior art, either singly or in combination, discloses or suggests the present invention.

BRIEF SUMMARY OF THE INVENTION

The present invention discloses a device that uses a squeeze bag-type resuscitator in a manner that allows a rescuer to combine artificial, emergency ventilation of a patient's lungs with cardiopulmonary resuscitation (CPR) type chest compressions.

It is an object of the present invention to provide a cardiopulmonary resuscitation device that combines a squeeze bag-type resuscitator and cardiopulmonary resuscitation (CPR) type chest compressions.

It is another object of the present invention to provide such a cardiopulmonary resuscitation device that incorporates pumping pure oxygen into the patient's lungs with the first squeeze of the squeeze bag-type resuscitator.

It is another object of the present invention to provide such a cardiopulmonary resuscitation device that incorporates pumping medicine into the patient's lungs with the first squeeze of the squeeze bag-type resuscitator.

It is another object of the present invention to provide such a cardiopulmonary resuscitation device that includes means for monitoring the amount of force being applied to the patient's chest.

It is another object of the present invention to provide such a cardiopulmonary resuscitation device that includes a backboard for keeping the patient's head tilted and airway open during chest compression and ventilation.

It is another object of the present invention to provide such a cardiopulmonary resuscitation device in which the backboard includes motorized means to provided repeated and rapid chest compression and forced ventilation.

BRIEF DESCRIPTION OF THE SEVERAL VIEWS OF THE DRAWINGS

FIG. 3 is a side elevational view of the cardiopulmonary resuscitation device of FIG. 1.

FIG. 4 is a top plan view of the self-inflating bag and a portion of the outlet port of the cardiopulmonary resuscitation device of FIG. 1.

FIG. 5 is a bottom plan view of the self-inflating bag and a portion of the outlet port of the cardiopulmonary resuscitation device of FIG. 1.

FIG. 6 is a top plan view somewhat similar to FIG. 4 but with portions of the self-inflating bag broken away to show the interior thereof with certain optional elements positioned within the self-inflating bag.

FIG. 11 is a side elevational view of a backboard for use with the cardiopulmonary resuscitation device of the present invention, with moved portions thereof shown in broken lines.

FIG. 12 is a top plan view of FIG. 11.

DETAILED DESCRIPTION OF THE INVENTION

Figure 1:
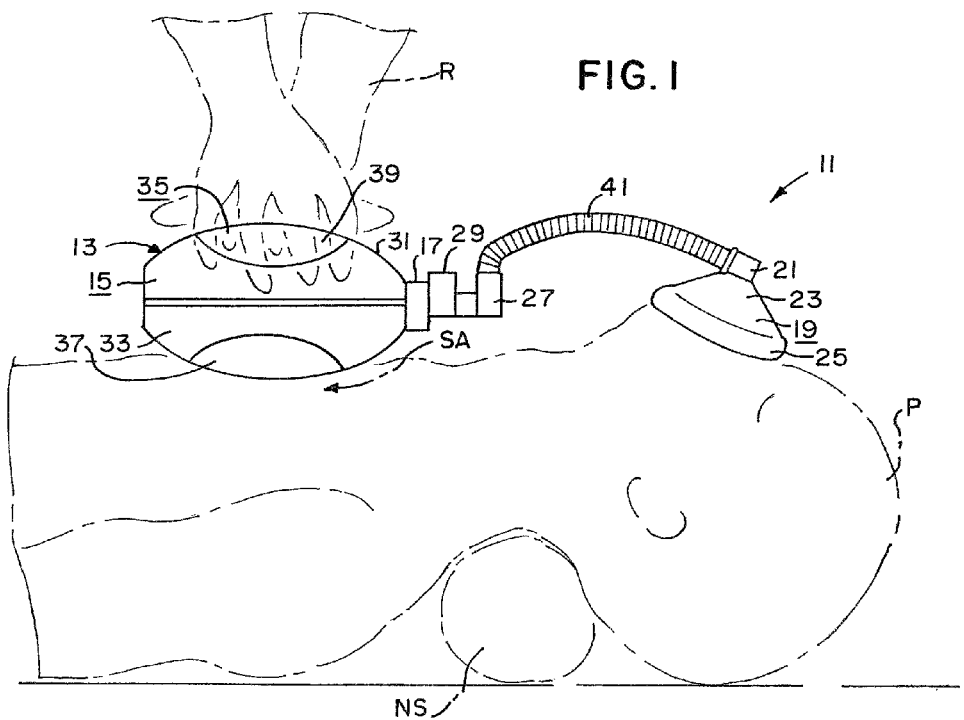
FIG. 1 is a somewhat diagrammatic view of a first embodiment of the cardiopulmonary resuscitation device of the present invention, shown with the face mask thereof placed over a patient's mouth and nose, and with the self-inflating bag thereof placed on the patient's chest with the target indicia on the self-inflating bag positioned over the patient's sternum area.
Figure 2:
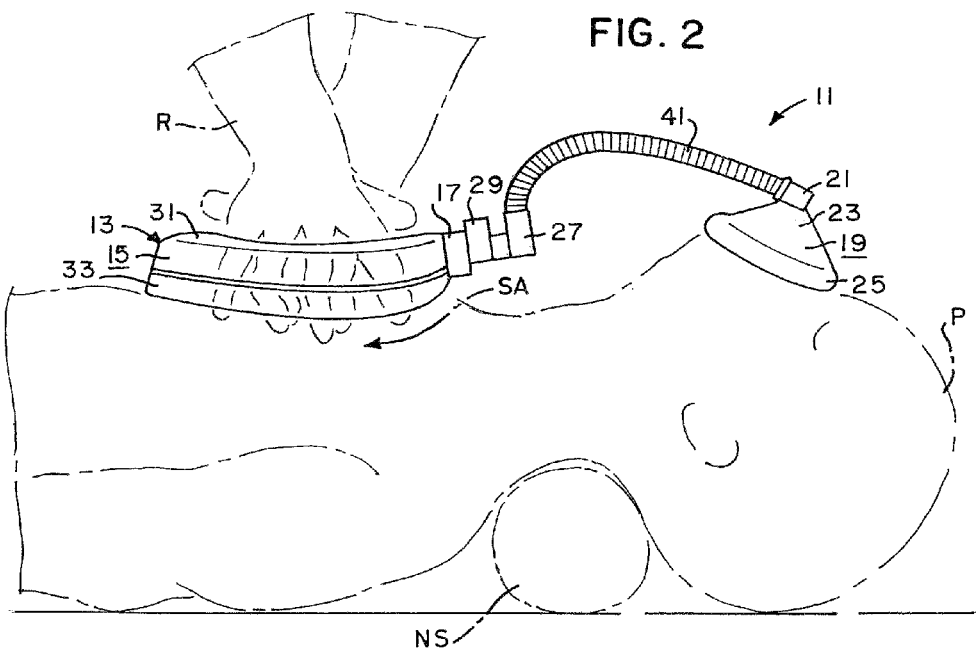
FIG. 2 is a somewhat diagrammatic view somewhat similar to FIG. 1 but with a rescuer compressing the self-inflating bag to ventilate the patient's lungs and compress the patient's sternum area.

A first embodiment of the cardiopulmonary resuscitation device of the present invention is shown generally in FIGS. 1-6, and identified by the numeral 11. The device 11 uses a modified squeeze bag-type resuscitator 13 in a manner that allows a user/rescuer R to help or rescue a patient P by combining artificial, emergency ventilation of the patient's lungs with cardiopulmonary resuscitation (CPR) type chest compressions on the patient's sternum area SA.

The squeeze bag-type resuscitator 13 preferably includes a typical self-inflating squeeze bag 15 constructed so that when the bag 15 is squeezed or otherwise compressed, air or oxygen is forced from the interior of the bag 15 out some type of outlet port or connector 17 for allowing the squeeze bag 15 to be connected to other parts of the resuscitator 13, e.g., to a face mask 19 for placement over a patient's mouth and nose. The face mask 19 (sometimes called a facepiece) typically includes a mount 21 for connection to the squeeze bag 15 or the like and a body 23 with a seal member 25 about the edge thereof to allow a substantially air-tight seal to be formed between the face mask 19 and the patient's face. The face mask 19 may also include an elastic head band or the like (not shown) for securing the body 23 thereof to the patient's face. The resuscitator 13 typically includes some type of escape valve 27 (often referred to as a nonrebreathing or NRB valve) mounted between the outlet port or connector 17 of the bag 15 and the face mask 19 so that after the face mask 19 is placed over the patient's mouth and nose, air from the patient's lungs will leave the face mask 19 through the escape valve 27 without returning to the bag 13. When the bag 15 is released, etc., it will re-inflate automatically, drawing atmosphere air, etc., into the bag through a bag fill valve 29 (i.e., a one way, inward flow check valve) that is combined with the bag 15 in communication with the interior thereof by being coupled to the connector 17 or attached directly to the bag 15, often at the end of the bag 15 directly opposite from the connector 17. While the shape and size of the bag 15 can vary as will now be apparent to those skilled in the art, in general, the bag 15 has one side that can be designated as the top side 31 and another side that can be designated as the bottom side 33.

The device 11 of the present invention includes target indicia 35 on the self-inflating bag 13 to indicate the proper position of the self-inflating bag 15 on the patient's sternum area SA and to indicate the proper location on the self-inflating bag 15 for applying force to the top side 31 of the self-inflating bag 15 in order to perform artificial, emergency ventilation of the patient's lungs followed by cardiopulmonary resuscitation (CPR) type chest compressions on the patient's sternum area SA. The target indicia 35 preferably includes a bottom target indicia 37 on the bottom side 33 of the self-inflating bag 15 to indicate the proper position of the self-inflating bag 15 on the patient's sternum area SA, and preferably includes a top target indicia 39 on the top side 31 of the self-inflating bag 15 to indicate the proper location on the self-inflating bag 15 for applying force to the top side 31 of the self-inflating bag 15 in order to perform artificial, emergency ventilation of the patient's lungs followed by cardiopulmonary resuscitation (CPR) type chest compressions on the patient's sternum area SA. While the specific construction, shape and size of the bottom and top target indicia 37, 39 can vary as will now be apparent to those skilled in the art, each bottom and top target indicia 37, 39 may consist merely of a visually and/or tactually distinctive, circular shaped decal, piece of tape, etc., attached to the appropriate surface of the bag 15.

The device 11 of the present invention includes a tube 41 extending from the outlet port 17 of the self-inflating bag 15 to the face mask 19 so that air forced out of the bag 13 through the outlet port 17 thereof will pass to the face mask 19 and into the patient's lungs when the face mask 19 is placed over the patient's mouth and nose. The tube 41 is preferably elongated and flexible for allowing the self-inflating bag 15 to be positioned over the patient's sternum area SA while the face mask 19 is placed over the patient's mouth and nose. While the exact size, length and construction of the tube 41 may vary as will now be apparent to those skilled in the art, the tube 41 may be constructed out of typical, medical grade, flexible plastic hose sized to fit the mount 21 of the face mask 19 and the escape valve 27, and long enough to extend between the patient's sternum area SA and face while allowing the bag 15 to be properly positioned on the patient's sternum area SA with the face mask 19 properly positioned simultaneously over the patient's nose and mouth. The tube 41 is preferably designed to retrofit through adaptable connectors any standard tracheobronchial tree or bronchial tube. This will allow a user/rescuer R to administer to the patient P who has been injected with a tracheobronchial tree or bronchial tube with the same method of cardiopulmonary resuscitation without the face mask 19.

The device 11 may include a quantity of pure oxygen 43, or high oxygen content air, within the bag 15 so that the quantity of pure oxygen 43 is forced into the patient's lungs the first time the bag 15 is squeezed after the face mask 19 is positioned over the patient's nose and mouth.

The device 11 may include a pharmaceutical composition 45 within the bag 15 so that the pharmaceutical composition 45 is forced into the patient's lungs the first time the bag 15 is squeezed after the face mask 19 is positioned over the patient's nose and mouth. The pharmaceutical composition 45 may consist of a single drug or chemical, or a combination of drugs or chemicals.

The device 11 may include release valve or seal (not shown) to keep the quantity of pure oxygen 43 and/or pharmaceutical composition 45 from leaking or exiting the self-inflating bag 15 until activated by the user/rescuer R.

The method of using the cardiopulmonary resuscitation device 11 of the present invention includes the step of first providing a cardiopulmonary resuscitation device 11 including a self-inflating bag 15, target indicia 35 on the self-inflating bag 15 to indicate the proper position of the self-inflating bag on the patient's sternum area SA and to indicate the proper location on the self-inflating bag 15 for applying force to the top side 31 of the self-inflating bag 15, a face mask 19 for placement over the patient's mouth and nose, and a tube 41 extending from the outlet port 17 of the self-inflating bag 15 to the face mask 19. The patient P is placed in a normal cardiopulmonary resuscitation position, preferably supine with a neck support NS for maintaining the patient's airway open during resuscitation. The face mask 19 of the cardiopulmonary resuscitation device 11 is placed over the patient's mouth and nose, and the self-inflating bag 15 of the cardiopulmonary resuscitation device 11 is placed on the patient's chest with the target indicia 35 on the self-inflating bag 15 positioned over the patient's sternum area SA. The user/rescuer R can then apply force to the target indicia 35 on the self-inflating bag 15 of the cardiopulmonary resuscitation device 11 to first force air from the self-inflating bag 15 through the tube 41 and the face mask 19 into the patient's lungs to ventilate the patient's lungs (often referred to as a rescue breath), and then to compress the patient's sternum area SA (often referred to as a chest compression). When the self-inflating bag 15 includes a quantity of pure oxygen 43, the step of applying force to the target indicia 35 to first force air from the self-inflating bag 15 into the patient's lungs to ventilate the patient's lungs also causes the quantity of pure oxygen 43 to be forced into the patient's lungs. When the bag 15 includes a pharmaceutical composition 45, the step of applying force to the target indicia 35 to first force air from the self-inflating bag 15 into the patient's lungs to ventilate the patient's lungs also causes the pharmaceutical composition 45 to be forced into the patient's lungs. After thus applying force to the target indicia 35 on the self-inflating bag 15 of the cardiopulmonary resuscitation device 11, the user/rescuer R releases the self-inflating bag 15, and the bag 15 re-inflates by drawing atmosphere air into the bag 15 through the bag fill valve 29, while air from the patient's lungs will pass to atmosphere through the escape valve 27. These cardiopulmonary resuscitation steps can be repeated as necessary. Typically, the user/rescuer R will apply a number of chest compressions after a single forced ventilation (rescue breath) by applying a number of chest compressions before fully releasing the self-inflating bag 15) so that the ratio of chest compressions to forced ventilations equal a desired number (e.g., 15 to 30 chest compressions per two forced ventilations at a rate of 80 to 100 compressions a minute). The cardiopulmonary resuscitation device 11 may include pressure sensors (not shown) to monitor chest compressions, and an audible means (not shown) that will orally walk a user/rescuer R through the steps of CPR using the device.

Figure 7:
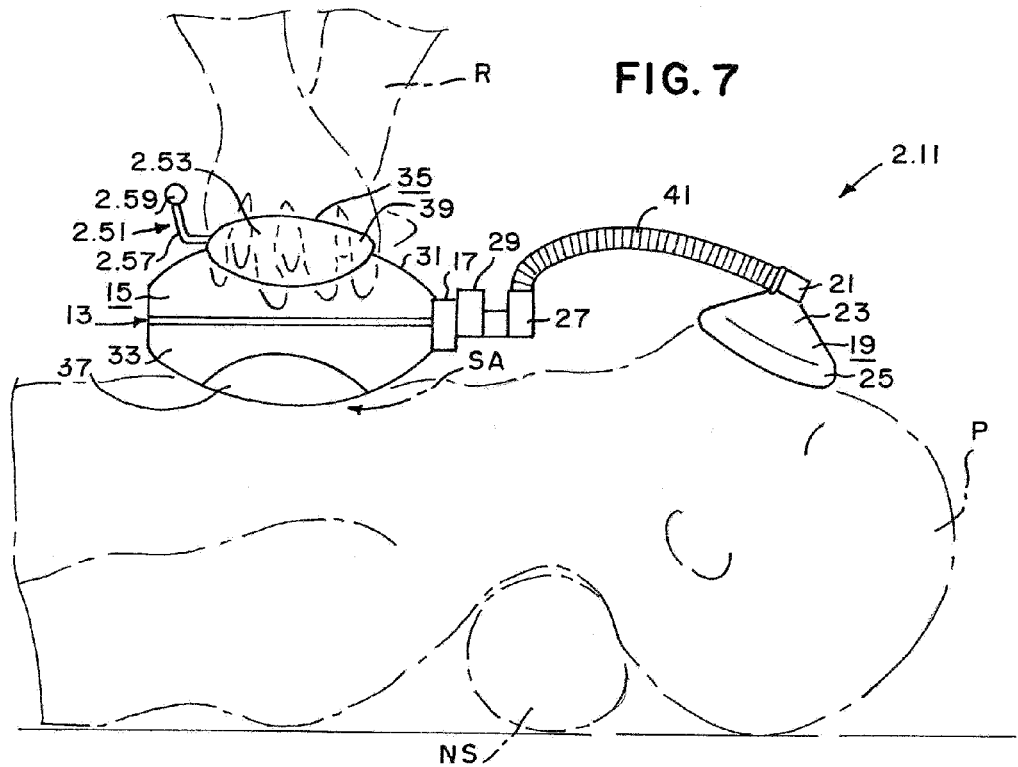
FIG. 7 is a somewhat diagrammatic view of a second embodiment of the cardiopulmonary resuscitation device of the present invention, shown with the face mask thereof placed over a patient's mouth and nose, and with the self-inflating bag thereof placed on the patient's chest with the target indicia on the self-inflating bag positioned over the patient's sternum area.
Figure 8:
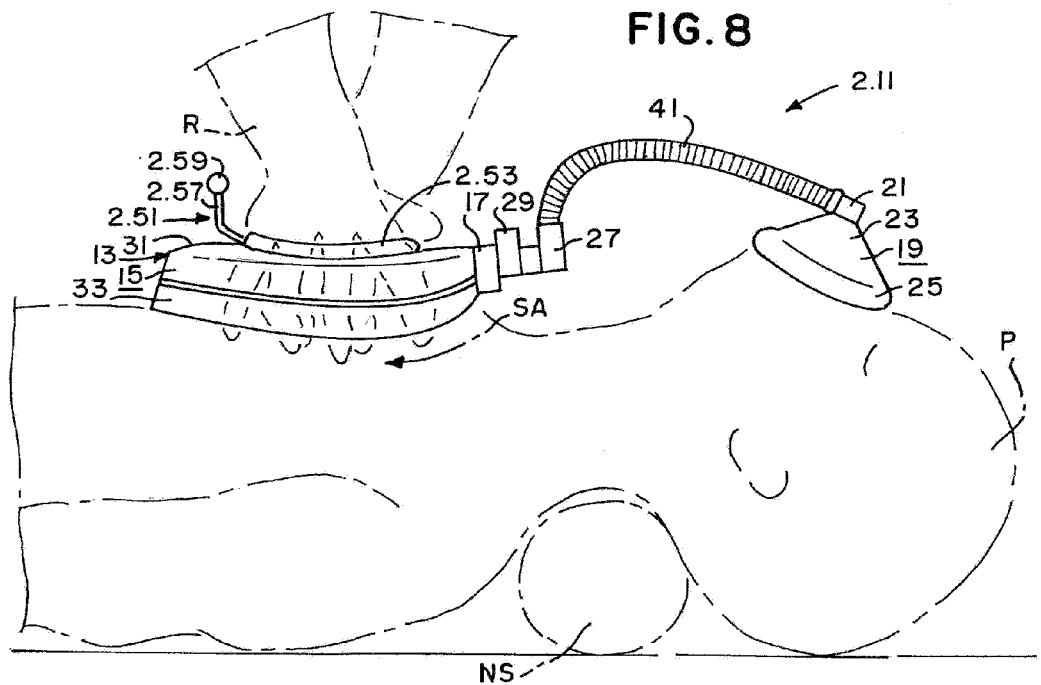
FIG. 8 is a somewhat diagrammatic view somewhat similar to FIG. 7 but with a rescuer compressing the self-inflating bag to ventilate the patient's lungs and compress the patient's sternum area.
Figure 9:
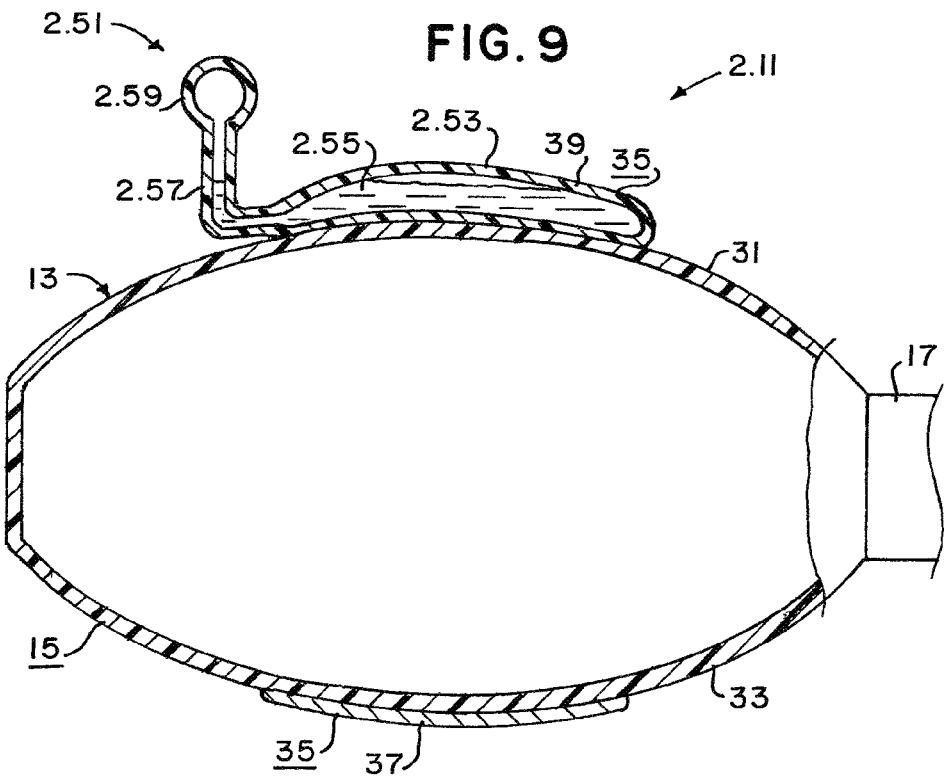
FIG. 9 is a side elevational view of the self-inflating bag of the cardiopulmonary resuscitation device of FIG. 7 with portions thereof broken away to show internal structure.
Figure 10:
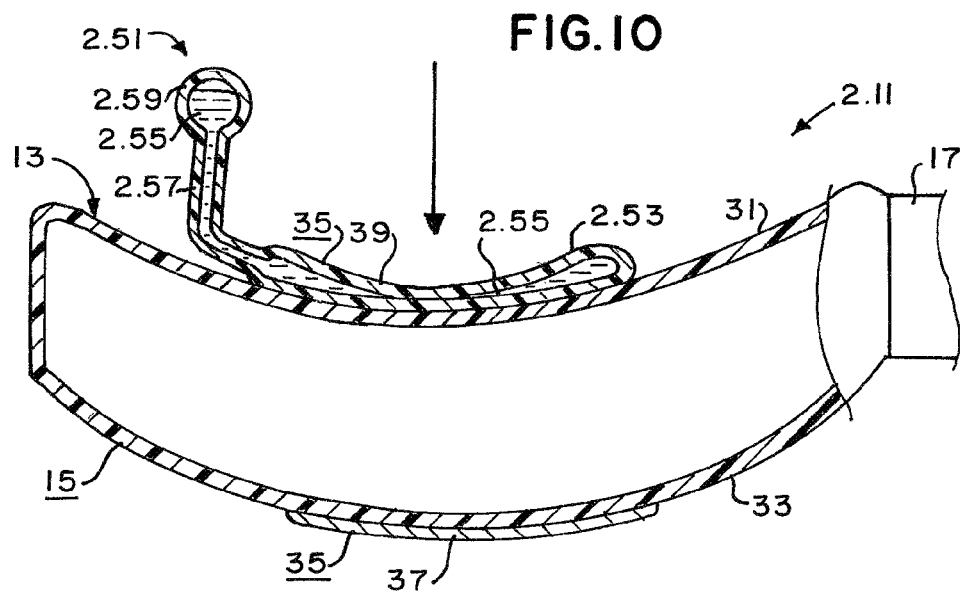
FIG. 10 is similar to FIG. 9 but showing the self-inflating bag thereof in a compressed state.

A second embodiment or modified version of the cardiopulmonary resuscitation device of the present invention is shown generally in FIGS. 7-10 and identified by the numeral 2.11. The cardiopulmonary resuscitation device 2.11 is substantially identical to the cardiopulmonary resuscitation device 11 and the above disclosure of the cardiopulmonary resuscitation device 11 should be consulted for a detailed understanding of the construction and operation of the cardiopulmonary resuscitation device 2.11 and the same reference numerals and characters will be used for like components of the cardiopulmonary resuscitation device 2.11 as herein used for the cardiopulmonary resuscitation device 11. However, as clearly shown in FIGS. 7-10, the cardiopulmonary resuscitation device 2.11 includes indicator means 2.51 for providing the user/rescuer R with an indicator of the amount of force being applied to the sternum area SA of the patient P when applying force to the target indicia 35 on the self-inflating bag 15 of the cardiopulmonary resuscitation device 2.11 during CPR. The indicator means 2.51 preferably includes a body or reservoir member 2.53 containing a quantity of fluid 2.55, and a tube member 2.57 extending from the body member 2.53 so that when force is applied to the body member 2.53 (i.e., when the user/rescuer R presses down on or otherwise applies force to the target indicia 35 on the self-inflating bag 15 of the cardiopulmonary resuscitation device 2.11), fluid 2.55 will be forced from the body member 2.53 up the tube member 2.57 a distance proportional to the amount of force applied to the body member 2.53 and the distance the patient's sternum area SA is compressed. The distal end of the tube member 2.57 may include a bulb 2.59 for receiving excess fluid 2.55 during a full compression. At least a portion of the tube member 2.57 and/or bulb 2.59 is preferably transparent to allow the fluid 2.55 to be easily seen therethrough. The body member 2.53 may be placed on or may actually form the top target indicia 39 of the target indicia 35 on the top side 31 of the self-inflating bag 15 as will now be apparent to those skilled in the art. The device 2.11 may include a hand-hold band or strap on the body member 2.53 or bag 15 (not shown) to allow the user/rescuer R to easily hold and control the body member 2.53 and bag 15 and to control the positioning of the hand on the top indicia 35, and also prevent the bag 15 from rolling out away from the user/rescuer R or away from the patient's sternum area SA, etc.

Figure 13:
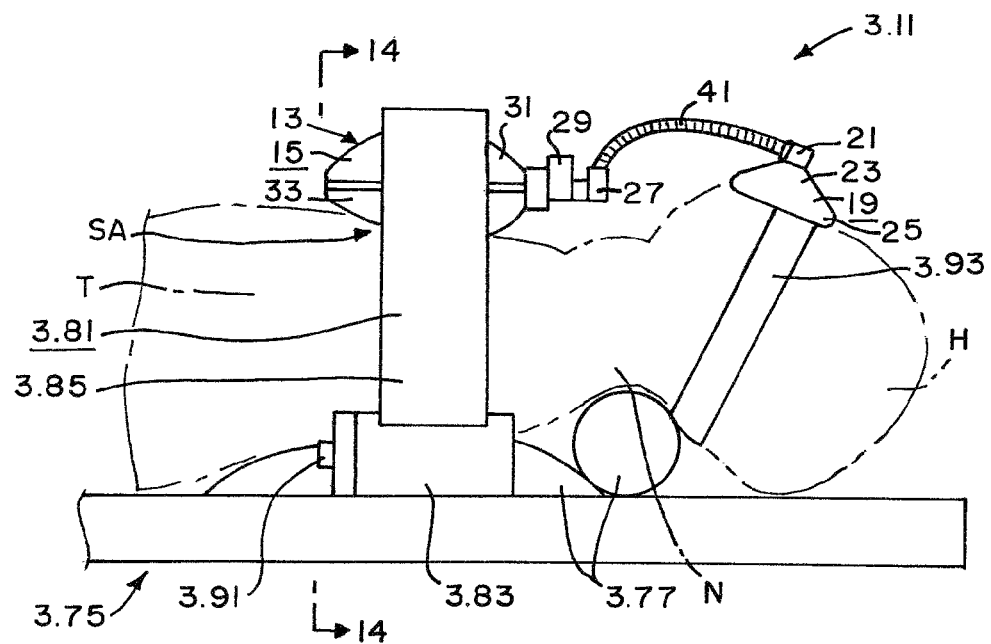
FIG. 13 is a side elevational view of the first embodiment of the cardiopulmonary resuscitation device of the present invention, shown with the face mask thereof placed over a patient's mouth and nose, with the self-inflating bag thereof placed on the patient's chest, with the patient's head and chest supported on the backboard of FIG. 11, and with a motorized compression means combined therewith.
Figure 14:
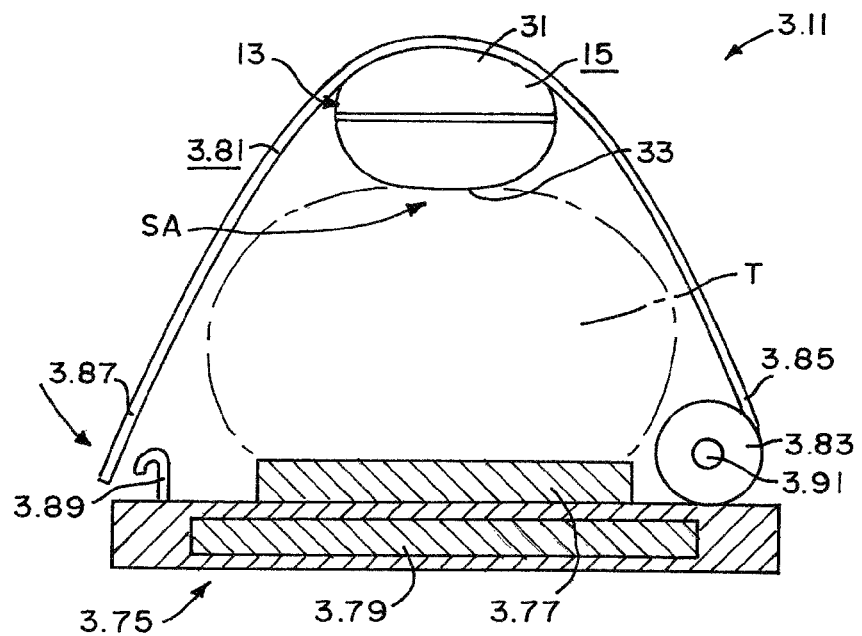
FIG. 14 is a sectional view substantially as taken on line 14-14 of FIG. 13.
Figure 15:
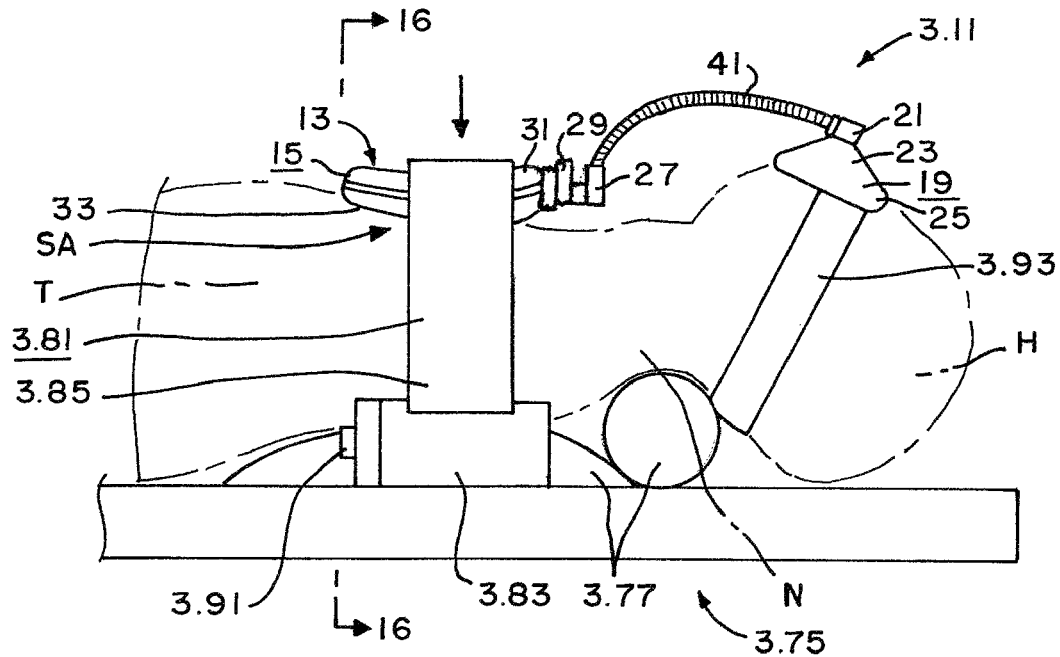
FIG. 15 is a side elevational view similar to FIG. 13 but showing the motorized compression means compressing the self-inflating bag to ventilate the patient's lungs and compress the patient's sternum area.
Figure 16:
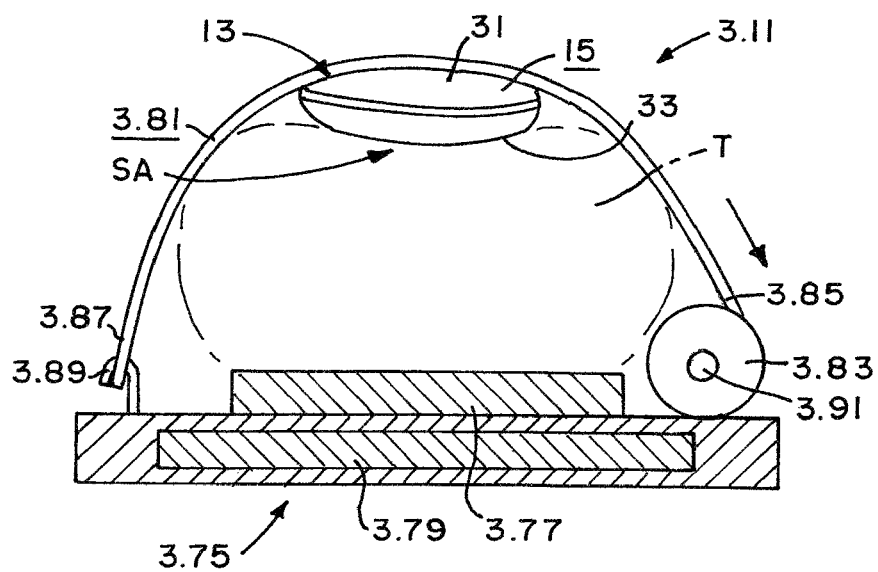
FIG. 16 is a sectional view substantially as taken on line 16-16 of FIG. 15.

A third embodiment or modified version of the cardiopulmonary resuscitation device of the present invention is shown generally in FIGS. 11-16, and identified by the numeral 3.11. The cardiopulmonary resuscitation device 3.11 is substantially identical to the cardiopulmonary resuscitation device 11 and the above disclosure of the cardiopulmonary resuscitation device 11 should be consulted for a detailed understanding of the construction and operation of the cardiopulmonary resuscitation device 3.11 and the same reference numerals and characters will be used for like components of the cardiopulmonary resuscitation device 3.11 as herein used for the cardiopulmonary resuscitation device 11. However, as clearly shown in FIGS. 11-16, the cardiopulmonary resuscitation device 3.11 includes a backboard 3.75 for supporting at least the upper torso T of the patient P. Positioning means 3.77 may be provided on the top surface of the backboard 3.75 for properly positioning the patient's head H, neck N, and upper torso T to keep the patient's head H tilted back and airway open during chest compression and ventilation. The positioning means 3.77 may consist of a pillow-like member mounted on the top or upper surface of the backboard 3.75. The backboard 3.75 may be sized to placed under the patient's head H, neck N, and upper torso T only, or may include an extension 3.79 for being pulled out to receive the patient's lower body. The backboard 3.75 may have openings 3.80 therethrough to provide hand holds and to allow the backboard 3.75 to be easily held and lifted with the patient P supported thereon. The backboard 3.75 includes a belt 3.81 for being placed over the self-inflating squeeze bag 15 and the patient's chest or sternum area SA, and includes motorized means 3.83 for repeatedly tightening and relaxing the belt 3.81 to provided repeated and rapid chest compression and forced ventilation. The belt 3.81 preferably includes a first end 3.85 for being attached to shaft or spool of the motorized means 3.83 so that rotation of the shaft or spool will reel in or reel out the belt 3.81, and a second end 3.87 for extending over the bag 15 and hooked or otherwise attached to an anchor 3.89 attached to the backboard 3.75 opposite the motorized means 3.83 so that when the belt 3.81 is reeled in, it will compress the bag 15, causing forced ventilation followed by chest compression. The motorized means 3.83 may be electrically or spring operated, etc., and preferably includes control means 3.91 for controlling the reeling in and reeling out of the belt 3.81. The control means 3.91 may be a simple manually operated switch or computer operated controller, etc. The device 3.11 may include a second belt (not shown) for exerting force evenly over the patient's entire thoracic cavity. The motorized means 3.83 is designed so that the two belts are never activated simultaneously. The activations can be controlled manually by the user/rescuer R, using a switch, or by a computer chip or computer system, etc. The motorized means 3.83 may be designed so that the belt 3.81 will first deflate the bag 15 to do a forced ventilation and then compress the bag 15 against the patient's sternum area SA to provide the designed compression, and then partially release and re-compress the bag 15 to provide the desired ratio of compressions to ventilations, etc. Further, as clearly shown in FIGS. 13 and 15, the cardiopulmonary resuscitation device 3.11 may include a wide elastic strap 3.93 for securing the face mask 19 about the patient's mouth and nose, etc. The strap 3.93 may be approximately one to three inches (2.54 to 7.62 centimeters) wide (i.e., approximately the width of the patient's ear).

Although the present invention has been described and illustrated with respect to a preferred embodiment and a preferred use therefor, it is not to be so limited since modifications and changes can be made therein which are within the full intended scope of the invention.

The invention claimed is:

1. A cardiopulmonary resuscitation device that combines artificial, emergency ventilation of a patient's lungs with chest compressions on the patient's sternum area, said cardiopulmonary resuscitation device comprising:
   (a) a self-inflating bag having a top side, a bottom side, and an outlet port through which the content of said self-inflating bag is forced when said top side of said self inflating bag is pushed toward said bottom side of said self-inflating bag;
   (b) a face mask for placement over the patient's mouth and nose;
   (c) a tube extending from said outlet port of said self-inflating bag to said face mask; and
   (d) target indicia on said self-inflating bag to indicate the proper position of said self-inflating bag on the patient's sternum area and to indicate the proper location on said self-inflating bag for applying force to said top side of said self-inflating bag to first force air from said self-inflating bag through said tube and said face mask into the patient's lungs to ventilate the patient's lungs, and then to compress the patient's sternum area; said target indicia including a bottom target indicia on said bottom side of said self-inflating bag to indicate the proper position of said self-inflating bag on the patient's sternum area, and including a top target indicia on said top side of said self inflating bag to indicate the proper location on said self-inflating bag for applying force to said top side of said self-inflating bag.

2. The cardiopulmonary resuscitation device of claim 1 in which said tube is elongated and flexible for allowing said self-inflating bag to be positioned over the patient's sternum area while said face mask is placed over the patient's mouth and nose.

3. The cardiopulmonary resuscitation device of claim 1 in which said self-inflating bag includes a quantity of pure oxygen.

4. The cardiopulmonary resuscitation device of claim 1 in which said self-inflating bag includes a pharmaceutical composition.

5. The cardiopulmonary resuscitation device of claim 1 in which is included indicator means for providing an indication of the amount of force being applied to said top side of said self-inflating bag.

6. A cardiopulmonary resuscitation device that combines artificial, emergency ventilation of a patient's lungs with chest compressions on the patient's sternum area, said cardiopulmonary resuscitation device comprising:
   (a) a self-inflating bag having a top side, a bottom side, and an outlet port through which the content of said self-inflating bag is forced when said top side of said self inflating bag is pushed toward said bottom side of said self-inflating bag;
   (b) a face mask for placement over the patient's mouth and nose;
   (c) a tube extending from said outlet port of said self-inflating bag to said face mask;
   (d) target indicia on said self-inflating bag to indicate the proper position of said self-inflating bag on the patient's sternum area and to indicate the proper location on said self-inflating bag for applying force to said top side of said self-inflating bag to first force air from said self-inflating bag through said tube and said face mask into the patient's lungs to ventilate the patient's lungs, and then to compress the patient's sternum area; said target indicia including a bottom target indicia on said bottom side of said self-inflating bag to indicate the proper position of said self-inflating bag on the patient's sternum area, and including a top target indicia on said top side of said self inflating bag to indicate the proper location on said self-inflating bag for applying force to said top side of said self-inflating bag; and
   (e) a backboard for supporting at least the upper torso of a patient; said backboard including positioning means for positioning the patient in such a way that the patient's head is tilted and airway is open.

7. A cardiopulmonary resuscitation device that combines artificial, emergency ventilation of a patient's lungs with chest compressions on the patient's sternum area, said cardiopulmonary resuscitation device comprising:
   (a) a self-inflating bag having a top side, a bottom side, and an outlet port through which the content of said self-inflating bag is forced when said top side of said self inflating bag is pushed toward said bottom side of said self-inflating bag;
   (b) a face mask for placement over the patient's mouth and nose;
   (c) a tube extending from said outlet port of said self-inflating bag to said face mask;
   (d) target indicia on said self-inflating bag to indicate the proper position of said self-inflating bag on the patient's sternum area and to indicate the proper location on said self-inflating bag for applying force to said top side of said self-inflating bag to first force air from said self-inflating bag through said tube and said face mask into the patient's lungs to ventilate the patient's lungs, and then to compress the patient's sternum area; said target indicia including a bottom target indicia on said bottom side of said self-inflating bag to indicate the proper position of said self-inflating bag on the patient's sternum area, and including a top target indicia on said top side of said self inflating bag to indicate the proper location on said self-inflating bag for applying force to said top side of said self-inflating bag; and
   (e) a backboard for supporting at least the upper torso of a patient; said backboard including a belt for being placed over said self-inflating bag and the patient's chest, and including motorized means for repeatedly tightening and relaxing said belt to provided repeated and rapid chest compression and force ventilation.

* * * * *